(12) United States Patent
Aderka et al.

(10) Patent No.: US 6,608,044 B1
(45) Date of Patent: Aug. 19, 2003

(54) INHIBITION OF TNF ACTIVITY

(75) Inventors: Dan Aderka, Tel Aviv (IL); Talma Eshed (Englender), Givatayim (IL)

(73) Assignee: Applied Research Systems ARS Holding N.V., Curacao (AN)

( * ) Notice: Subject to any disclaimer, the term of this patent is extended or adjusted under 35 U.S.C. 154(b) by 0 days.

(21) Appl. No.: 09/623,225

(22) PCT Filed: Dec. 30, 1999

(86) PCT No.: PCT/IL99/00709

§ 371 (c)(1),
(2), (4) Date: Nov. 20, 2000

(87) PCT Pub. No.: WO00/40225

PCT Pub. Date: Jul. 13, 2000

(30) Foreign Application Priority Data

Dec. 30, 1998 (IL) .................................................. 127851

(51) Int. Cl.[7] ............................................. A61K 31/727
(52) U.S. Cl. .............................. 514/56; 514/2; 514/825; 536/21; 536/54
(58) Field of Search .............................. 514/56, 825, 2; 536/21, 54

(56) References Cited

U.S. PATENT DOCUMENTS 5,474,987 A * 12/1995 Cohen et al. .................. 514/56

FOREIGN PATENT DOCUMENTS

| WO | 92 19249 | 11/1992 |
| WO | WO 94/06476 A1 * | 3/1994 |
| WO | 99 09051 | 2/1999 |

OTHER PUBLICATIONS

Olsson et al., "Tumour necrosis factor (TNF) binding proteins (soluble TNF receptor forms) with possible roles in inflammation and malignancy", Eur. Cytokine Netw., vol. 4, No. 3, pp. 169–180, Jun. 1993.*

Kepros et al., "Mechanism of the Beneficial Effects of a Novel Nonanticoagulant Heparin (GM 1892) Following Hemorrhagic Shock: Down–Regulation of Proinflammatory Cytokine (TNF and IL–6) Production", *Sepsis and Shock*, pp.87–89, (1995).

Olsson et al., "Tumour necrosis factor (TNF) binding proteins (soluble TNF receptor forms) with possible roles in inflammation and malignancy", *Eur. Cytokine Netw.*, 4:(3):169–180, (1993).

Brazier et al., "Effect of Heparin on Interleukin–6 and Tumor Necrosis Factor β Serum Levels in Inflammatory Bowel Disease", *Immunology, Microbiology, and Inflammatory Disorders*, pp. A871, (1996).

Baram et al., "Inhibitory effects of low molecular weight heparin on mediator release by mast cells: preferential inhibition of cytokine production and mast cell–dependent cutaneous inflammation", *Clin Exp. Immunol.*, 110:485–491, (1997).

Imiela et al., "Oral Heparin in the Treatment of Rheumatoid Arthritis", *Archivum Immunologiae et Therapiae Experimentalis*, 43:313–315 (1995).

Abstract Aderka, "The potential biological and clinical significance of the soluble tumor necrosis factor receptors", *Cytokine & Growth Factor Reviews*, 7:(3):231–240, (1996).

Abstract, WO95/03827, "Method for Treating Multiple Sclerosis", Publication Date Feb. 9, 1995.

Abstract, WO94/06476, "Method of Treating TNF–Dependent Inflammation Using Tumor Necrosis Factor Antagonists", Publication Date Mar. 31, 1994.

Abstract, EP0512528, "Pharmaceutical compositions comprising and anticytokine" Publication Date Nov. 11, 1992.

* cited by examiner

*Primary Examiner*—Dwayne C. Jones
(74) *Attorney, Agent, or Firm*—Browdy and Neimark, P.L.L.C.

(57) ABSTRACT

The bioactivity of TNF is inhibited by administering heparin or a derivative thereof along with a soluble TNF receptor. The heparin or derivative thereof can be administered simultaneously with the soluble TNF receptor, either in separate compositions or in compositions containing both heparin or a derivative thereof and at least one soluble TNF receptor. The heparin or derivative may also be administered without the soluble TNF receptor and still effect some amount of inhibition of TNF bioactivity.

13 Claims, 12 Drawing Sheets

Interactions between TNF, soluble TNF-Receptors and Heparin or Low Molecular Weight Heparin

The equilibrium between TNF and its soluble receptors

Receptor bound TNF     Trimeric, free active TNF     Monomeric inactive TNF

Legend

▼ TNF (trimer)

▽ TNF (monomer)

○ Soluble TNF receptors (p55/p75)

INHIBITION OF TNF ACTIVITY

CROSS REFERENCE TO RELATED APPLICATION

The present application is the national stage under 35 U.S.C. 371 of PCT/IL99/00709, filed Dec. 30, 1999.

FIELD OF THE INVENTION

The present invention is directed to a method and pharmaceutical compositions for inhibiting activity of tumor necrosis factor (TNF).

BACKGROUND OF THE INVENTION

Tumor necrosis factor (TNF) is a pro-inflammatory cytokine produced by a wide spectrum of cells. It has a key role in defending the host, mediating complex cellular responses of different, and even contrasting, nature (Aggarwal et al, 1996). In excess, TNF may have detrimental systemic effects. Two specific high affinity cell surface receptors, the p55 TNF-receptor (p55 TNF-R) and the p75 TNF-receptor (p75 TNF-R), function as transducing elements, providing the intracellular signal for cell responses to TNF. The extracellular parts of the TNF-Rs, known as soluble TNF-Rs, were formerly referred to as TBP-I and TBP-II respectively (see Wallach, U.S. Pat. No. 5,359,037 and Tartaglia et al., 1992; Loetscher et al., 1991).

The biological effects of TNF depend upon its concentration and site of production. At low concentrations. TNF may produce desirable homeostatic and defense functions. For example, these effects may destroy tumor cells or virus infected cells and augment antibacterial activities of granulocytes. In this way, TNF contributes to the defense of the organism against infectious agents and to recovery from injury. However, at higher concentrations, systemically or in certain tissues, TNF can synergize with other cytokines, notably interleukin-1, to aggravate many inflammatory responses. Additionally, the effects of TNF-α, primarily on the vasculature, are now known to be a major cause for symptoms of septic shock (Tracey et al, 1986). In some diseases, TNF may cause excessive loss of weight (cachexia) by suppressing activities of adipocytes and by causing anorexia.

TNF has been found to induce the following activities (together with interleukin-2): fever, slow-wave sleep, hemodynamic shock, increased production of acute phase protein, decreased production of albumin, activation of vascular endothelial cells, increased expression of major histocompatibility complex molecules, decreased lipoprotein lipase, decreased cytochrome P450, decreased plasma zinc and iron, fibroblast proliferation, increased synovial cell collagenase, increased cyclo-oxygenase activity, activation of T cells and B cells, and induction of secretion of the cytokines, TNF itself, interleukin-1 and interleukin-6.

Because of its pleiotropic effects, TNF has been implicated in a variety of pathologic states in many different organs of the body. In blood vessels, TNF promotes hemorrhagic shock, down-regulates endothelial cell thrombomodulin, and enhances a procoagulant activity. It causes adhesion of white blood cells, and probably of platelets, to the walls of blood vessels, and so may promote processes leading to atherosclerosis, as well as to vasculitis.

TNF activates blood cells and causes the adhesion of neutrophils, eosinophils, monocytes/macrophages and T and B lymphocytes. By inducing interleukin-6 and interleukin-8, TNF augments the chemotaxis of inflammatory cells and their penetration into tissues. Thus, TNF has a role in the tissue damage of autoimmune disease, allergies and graft rejection.

TNF has also been called cachectin because it modulates the metabolic activities of adipocytes and contributes to the wasting and cachexia accompanying cancer, chronic infections, chronic heart failure and chronic inflammation. TNF may also have a role in tissue damage of autoimmune diseases, allergies, and graft rejection.

TNF also has metabolic effects on skeletal and cardiac muscle. It also has marked effects on the liver: it depresses albumin and cytochrome P450 metabolism and increases production of fibrinogen, α-Acid Glycoprotein (AGP) and other acute phase proteins. It can also cause necrosis of the bowel.

In the central nervous system, TNF crosses the blood-brain barrier and induces fever, increased sleep and anorexia. Increased TNF concentration is also associated with multiple sclerosis. It also causes adrenal hemorrhage and affects production of steroid hormones, enhances collagenase and PGE-2 in the skin, and causes the breakdown of bone and cartilage by activating osteoclasts.

Thus, TNF is involved in the pathogenesis of many undesirable inflammatory conditions, in autoimmune disease, graft, rejection, vasculitis and atherosclerosis. It appears to have a role in heart failure, in the response to cancer and in anorexia nervosa. For these reasons, means have been sought to inhibit the activity of TNF as a way to control a variety of diseases.

While exploring ways for antagonizing the destructive potential of TNF in certain clinical conditions, investigators looked for natural TNF inhibitors (Engelmann et al, 1989; Engelmann et al, 1990; Seckinger et al, 1989; Olsson et al, 1989). Such agents, first detected in urine, were structurally identical to the extracellular cytokine binding domains of the two membrane associated TNF-Rs (Nophar et al, 1990). These shed soluble TNF-Rs (sTNF-Rs) can compete for TNF with the cell surface receptors and thus block the cytokine activity.

However, interactions between the TNF-Rs and their ligand are much more complex than initially thought. At physiological concentrations, the trimeric and bioactive TNF molecules decay, dissociating into inactive monomeric forms (Petersen et al, 1989; Aderka et al, 1992). Addition of sTNF-Rs to the TNF trimers promotes formation of complexes between them, which can preserve and prevent the decay of the active, trimeric forms of TNF (Aderka et al, 1991; De Groote et al, 1993). This bioactive TNF may dissociate from this complex to replace free TNF which decayed, thus maintaining a constant concentration of free, bioactive, trimeric cytokine. This reversible interaction between the soluble receptors and their ligand expands the functions attributable to the TNF receptors. In their soluble form, the TNF-Rs may serve as:

(a) TNF antagonists (when present in large excess relative to TNF);

(b) TNF carrier proteins (between body compartments);

(c) slow release reservoirs for bioactive TNF;

(d) stabilizers of the TNF's bioactive form (which may also prolong the half-life of TNF); and (e) TNF "buffers", by inhibiting the effects of high TNF concentrations and presenting it at low and well-controlled levels to the cells (Aderka et al, 1992).

The functions of the TNF receptors, thus, are not limited to signal transduction but include, in their soluble forms, extracellular regulatory roles affecting local and systemic bioactive TNF availability.

TNF and Disease

Examination of patients with septic shock due to meningococcemia revealed that the ratio of TNF/sTNF-Rs was higher in patients with a fatal outcome compared to patients who recovered, suggesting a critical imbalance between the ligand and its inhibitors (Girardin et al, 1994). Neutralization of the excess TNF seemed to be the preferred next step.

Indeed, dimeric Fc fusion constructs of the p55 sTNF-R, but not of the p75 sTNF-R, were found to protect mice from lethal doses of LPS (Evans et al, 1994) if administered not later than 1–3 hours post LPS (Peppel et al, 1991; Mohler et al, 1993; Ashkenazi et al, 1991; Lesslauer et al, 1991). This suggests that septic shock manifestations occur if the initial high TNF concentrations generated are not buffered by adequate soluble receptor concentrations during that narrow window of time.

To add to the growing confusion, neutralization of TNF with monoclonal anti-TNF Ab (Abraham et al, 1995; Kaul, et al, 1996) or p55 sTNF-R IgG1 (Leighton et al, 1996) in patients with severe sepsis or septic shock yielded conflicting results. In one study, the antibodies proved ineffective (Abraham et al, 1995), while in the other, administration of the antibodies benefited only those patients with baseline interleukin-6 levels higher than 1000 pg/ml but increased the mortality of those with lower interleukin-6 levels (Kaul et al, 1995). In another randomized trial, septic patients given a recombinant dimer consisting of sTNF-R/Fc portion of IgG1 had higher mortality (48–53%) as compared to placebo-treated patients (30%) (Suffredini et al, 1994; Fisher et al, 1996). Interestingly, the higher the dose of the sTNF-Rs administered, the higher was the patient mortality (Fisher et al, 1996). It was suspected that the effective removal of circulating TNF may result in the exacerbation of the systemic infection (Fisher et al, 1996). In contrast, in a recent study the administration of similar soluble Fc receptor constructs apparently benefitted septic patients irrespective of their serum interleukin-6 concentrations, with a 36% mortality reduction compared to placebo treated individuals (Leighton et al, 1996). These contradictory data give the impression that the administration of sTNF-Rs may have a very narrow therapeutic index which would be difficult to individualize at bedside. Too much of the receptors may totally neutralize TNF, exacerbating the systemic infection, while too little of the receptors may not neutralize enough TNF, resulting in septic shock and the patient's demise. The real challenge is to fine-tune the sTNF-R dose in order to permit low TNF levels to exert their protective effects. Thus, paradoxically, lower doses of sTNF-Rs than previously employed (Fisher et al, 1996), rather than higher ones, may benefit septic shock patients.

Since the TNF neutralization should not be complete, but should be aimed to leave low amounts of bioactive TNF to exert the desired beneficial effects, natural soluble TNF receptors may be ideally suited for this purpose.

TNF is also a pivotal cytokine in the pathogenesis of Crohn's Disease, a chronic and disabling disorder of the bowel, and is, therefore, a prime target for specific immunotherapy (Braegger et al, 1992; MacDonald et al, 1990; Breese et al, 1994). Indeed, treatment of Crohn's Disease patients with chimeric anti-TNF monoclonal antibodies induced a spectacular remission in patients unresponsive to conventional therapy (van Dullemen et al, 1995). Whether slow release preparations of sTNF-Rs (Eliaz et al, 1966) will have identical effects on the course of this disease remains to be determined.

In another autoimmune disorder, rheumatoid arthritis, it was demonstrated that the serum sTNF-Rs may be useful in monitoring disease activity (Cope et al, 1992; Roux-Lombard et al, 1993). It was shown that despite the presence of high levels of TNF inhibitors in joints affected by rheumatoid arthritis, these inhibitors were insufficient to neutralize TNF activity (Cope et al, 1992). A randomized double blind study comparing administration of chimeric anti-TNF monoclonal antibodies to patients with rheumatoid arthritis resulted in an impressive clinical remission (Levine et al, 1994). Recently, it was demonstrated that incorporation of the sTNF-Rs into polymeric systems, such as ethylene-vinyl acetate copolymers or polylactic-glycolic acid and their subcutaneous injection, can provide systemic natural p55 sTNF-Rs at high concentrations, at a constant rate for prolonged periods (more than one month) (Eliaz et al, 1966). It is thus possible that sTNF-Rs will prove therapeutically effective in treating rheumatoid arthritis as well.

TNF, TNF-Rs and the Heart

Elevated concentrations of TNF and its soluble receptors have been detected in sera of patients with heart failure (Levine et al, 1990). TNF may contribute to the impaired myocardial contraction in this condition as it was shown to produce a significant depression of myocyte shortening (Cunnion, 1990). Furthermore, whole hearts perfused with serum from animals treated with TNF 18–22 hours earlier, exhibited significant impairment and decreased rate of relaxation compared to controls (DeMeules et al, 1992). Similar myocardial depressing effects may possibly be inflicted by continuous exposure of the heart to TNF, circulating in heart failure patients (Levine et al, 1990). Neutralization of the cytokine with sTNF-Rs may be useful in managing heart failure.

Inhibition of TNF

Heparin has been reported to bind TNF (Lantz et al, 1991). However, the significance of this observation was never examined. The effects of heparin seem to be the exact opposite of the effects of TNF, as shown by Table I in Lantz et al.

SUMMARY OF THE INVENTION

The present invention provides for the use of heparin, and/or a derivative thereof, in the preparation of a pharmaceutical composition for inhibiting the bioactivity of TNF.

The present invention also provides pharmaceutical compositions for inhibiting the bioactivity of TNF.

The invention provides further a kit for the simultaneous or sequential administration of such a composition, comprising the active ingredients together with a pharmaceutically acceptable carrier, and instructions for use.

Heparin and low molecular weight heparins have been found to inhibit the cytokine bioactivity of TNF, particularly when acting with another TNF binding protein. Heparin is a natural TNF binding protein, and probably cross-links TNF to its p55 TNF and p75 TNF-receptors. This inhibits the cytokine bioactivity of TNF by presumably interfering with trimerization of the TNF receptors. The inventors raise the above theory of action without being bound thereby. Thus, by administering heparin or a derivative thereof along with a soluble TNF receptor, the bioactivity of TNF is inhibited, and the disorders caused by excess TNF can be successfully treated. The heparin or derivative thereof can be administered simultaneously with the TNF receptor, either in separate compositions or in compositions containing both heparin or a derivative thereof and at least one soluble TNF receptor.

DETAILED DESCRIPTION OF THE INVENTION

Figure 1A:
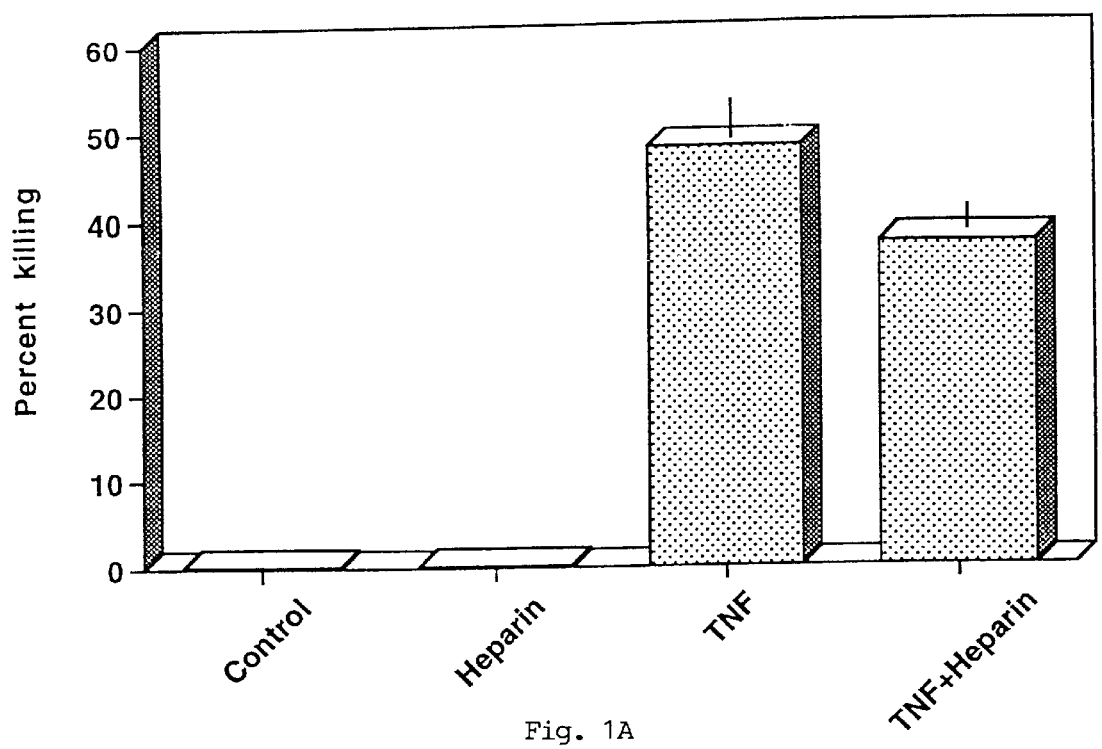
FIGS. 1A and 1B are graphs showing inhibition of TNF activity by heparin (FIG. 1A) and Clexane® (FIG. 1B).

It has been discovered that heparin or low molecular weight heparin is able to enhance the effect of sTNF-Rs, apparently in a synergistic rather than merely an additive manner.

Heparin is a glycosaminoglycan, a highly sulfated mucopolysaccharide, consisting of a heterogeneous series of repeating disaccharide units composed of D-glucuronic or L-iduronic acids in a 1,4-glycosidic linkage to glucosamine. Each of the repeating units contains two sulfate esters and one N-sulfate group. Heparin is the strongest anionically charged organic acid substance ever isolated from a living biological system. Heparin occurs in many different body tissues, but the lung, intestinal tract, liver, and mast cells are particularly rich in heparin. Heparin is a family of linear polymers that differ in chain length and molecular weight, and its precise complete composition is unknown.

Commercially, heparin is extracted from animal tissues, most commonly from bovine lungs and the intestinal mucosa of bovine, ovine, porcine, and caprine species. In any vial of therapeutically employed heparin, a wide range of molecular species, ranging from 2,000 to 25,000 daltons, are present. The potency of heparin is defined in units, where one unit is the amount of heparin that will prevent the coagulation of sheep plasma by the process of recalcification. Various extracts of heparin may range in potency, i.e., 1 mg by weight may range in potency from 80–170 units. The World Health Organization maintains reference standards for heparin.

Heparin exhibits its inhibitory effect on the blood coagulation cascade scheme by at least two different mechanisms. First, when heparin complexes with lysine residues of antithrombin III at high affinity in a 1:1 stoichiometric manner, the serine protease inhibitory effect of antithrombin III is enhanced several fold. Second, because of its high polyanionic charge density, heparin is able to neutralize the effect of positively charged activated glycoprotein coagulant serine proteases. Heparin also induces lipoprotein lipase and histaminase degradation of histamine, and has antiinflammatory properties as well.

Heparin has been widely used since the mid-1940s primarily for the prophylactic prevention and treatment of thrombotic diseases such as deep vein thrombosis, pulmonary emboli, and myocardial infarction. Another principal use of heparin is to prevent blood coagulation in extra-corporeal systems, thus making possible renal dialysis; cardiac bypass surgery; cardiac, pulmonary, hepatic, and renal transplantation; extra-corporeal pulmonary bypass oxygenation; and extra-corporeal circulatory membrane ultrafiltration. Low doses of low molecular weight heparin are used for the prophylactic prevention of intravascular thrombus formation. Heparin fragments, peptides, and synthetically prepared peptides have also been used.

In animal models, heparin has been shown to reduce the ability of autoimmune T lymphocytes to reach their target organ (Lider et al, 1990). Heparin has also been shown to suppress experimental autoimmune diseases in rats and to prolong the allograft survival in a model of skin transplantation in mice, when used in low doses of about 5 micrograms for mice and 20 micrograms for rats, injected once a day (Lider et al, 1989).

The mechanisms behind the observed effects of heparin are believed to involve inhibition of release by T lymphocytes of the enzyme(s) necessary for penetration of the vessel wall, primarily the enzyme heparanase that specifically attacks the glycosaminoglycan moiety of the sub-endothelial extracellular matrix that lines blood vessels (Naparstek et al, 1984). Expression of the heparanase enzyme is associated with the ability of autoimmune T lymphocytes to penetrate blood vessel walls and to attack the brain in the model disease experimental autoimmune encephalomyelitis.

Low molecular weight heparins, with an average molecular weight of 3000–6000, such as, for example, the low molecular weight heparins disclosed in European Patent EP 0014184, are derived from heparin. Some low molecular weight heparins are commercially available under different trade names, such Fragmin®, cf. U.S. Pat. No. 4,303,651, Fraxiparin®, Fraxiparine®, U.S. Pat. Nos. 4,486,420 and 4,692,435, Lovenox®, European Patent 40144, and Clexane®, U.S. Pat. No. 3,948,917.

Low molecular weight heparins can be produced in several different ways: enrichment by fractionalization by ethanol and/or molecular sieving, e.g., gel filtration or membrane filtration of the low molecular weight heparin present in standard heparin and controlled chemical (by nitrous acid, wbw-elimination, or periodiate oxidation) or enzymatic (by heparinase) depolymerization. The conditions for depolymerization can be carefully controlled to yield products of the desired molecular weights. Nitrous acid depolymerization is commonly used. Also, the benzylic ester of heparin can be depolymerized by wbw-elimination, which yields the same type of fragments as enzymatic depolymerization using heparinases. Low molecular weight heparin with low anticoagulant activity which retains the basic chemical structure of heparin can be prepared by depolymerization using periodate oxidation or by removing the antithrombin-binding fraction of low molecular weight heparin, prepared by other methods, using immobilized antithrombin for adsorption.

Fragmin® is a low molecular weight heparin with average molecular weight within the range of 4000–6000 dalton, produced by controlled nitrous acid depolymerization of sodium heparin from porcine intestinal mucosa. It is manufactured by Kabi Phannacia, Sweden, under the name Fragmin® for use as an antithrombotic agent as saline solutions for injection in single dose syringes of 2500 IU/0.2 ml and 5000 IU/0.2 ml, corresponding to about 16 mg and 32 mg., respectively.

Fraxiparin® and Fraxiparine® are low molecular weight heparins with average molecular weight of approximately 4500 dalton, produced by fractionation or controlled nitrous acid depolymerization, respectively, of calcium heparin from porcine intestinal mucosa. These low molecular weight heparins are manufactured by Sanofi (Choay Laboratories) for use as an antithrombotic agent in single doses comprising about 36 mg., corresponding to 3075 IU/0.3 ml water.

Lovenox®(Enoxaprain/e), a low molecular weight heparin fragment produced by depolymerization of sodium heparin from porcine intestinal mucosa using wbw-elimination, is manufactured by Pharmuka SF, France, and distributed by Rhone-Poulenc under the names Clexane® and Lovenox® for use as antithrombotic agents in single dose syringes comprising 20 mg/0.2 ml and 40 mg/0.4 ml water.

Low molecular weight heparins, produced by fractionalization or controlled depolymerization of heparins, show improved antithrombotic performance but also different pharmacokinetic properties as compared to heparin. The half-life is doubled and the bioavailbailty is higher with respect to their anticoagulant effect following subcutaneous injection (Bratt et al, 1985; Bone et al, 1987).

The properties of the low molecular weight heparins described above are a common feature to all low molecular weight heparins, regardless of the manufacturing process, the structural differences (created by depolymerization or those dependent on variation in the heparin used as raw material) or the anticoagulant activity, provided the low molecular weight heparin used is capable of inhibiting TNF secretion in vitro by resting T cells and/or macrophages in response to activation by contact with specific antigens, mitogens, disrupted extracellular matrix or its protein components, such as fibronectin or laminin.

To test the effectiveness of inhibition of activity of TNF (see Examples 1 and 2), WISH cells were seeded at a concentration of 30,000 cells per well in 100 µl medium. Sixteen hours later, when the cells had reached about 90% confluence, TNF, receptors, heparin, or Clexane® were added to the wells. The final concentrations added to the respective wells are as follows:

TNF 0.5 ng/ml

Heparin, 1 unit/ml

Clexane®, 1 unit/ml

TBPI (p55 TNF-receptor), 5 ng/ml

TBPII (p75 TNF-receptor), 10 ng/ml

The different combinations were mixed in an Eppendorf tube reaching a final volume of 300 µl. Then, 50 µl were added to the respective well. If incubation was required, it was conducted in the Eppendorf tube for 30 minutes at 37° C., in a mixture or separately. After each of the different combinations were added, 50 µl cycloheximide was added to each well. Sixteen hours later, the cell supernatants were discarded and neutral red dye was added for one hour at 37° C. The dye was extracted from surviving cells with a Sorensen's solution and the results were read in an ELISA reader.

Figure 1B:
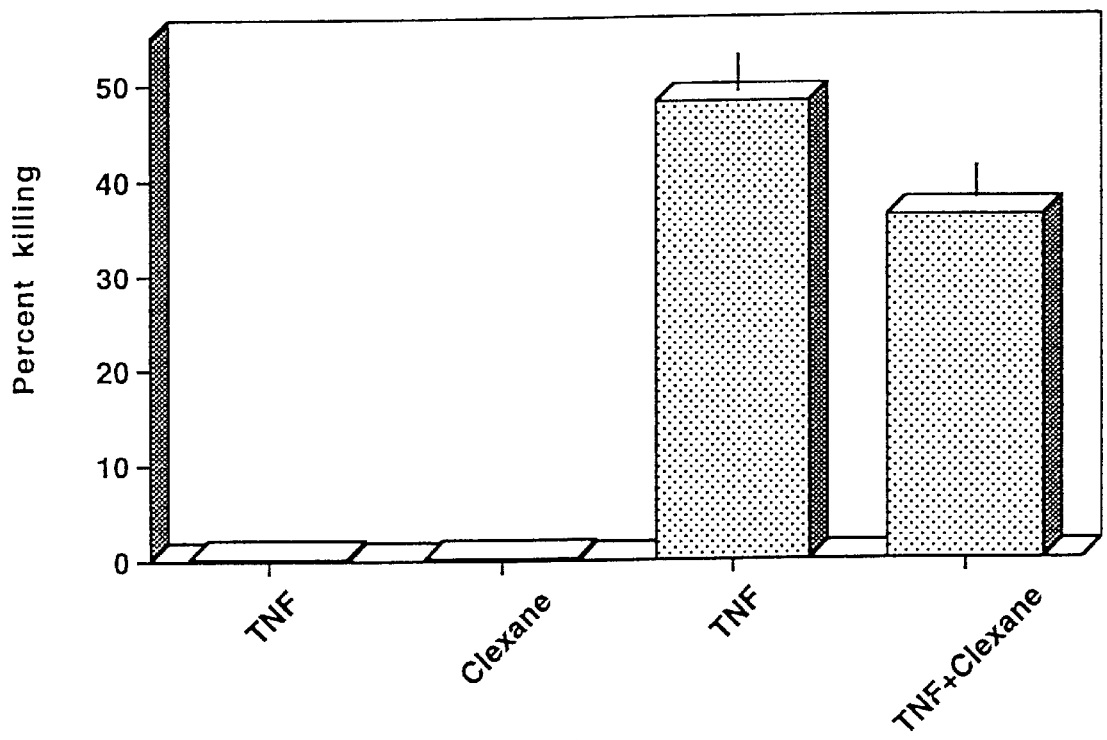

The addition of one unit/ml of heparin to 0.5 ng/ml of TNF was found to have about 25% of the bioactivity of TNF (i.e., a reduction of cytotoxicity from 49% to 37%), as shown in FIG. 1A. Clexane® had a very similar effect, as shown in FIG. 1B. Thus, both heparin and Clexane®, a low molecular weight heparin, inhibited the toxicity of TNF.

Figure 2:
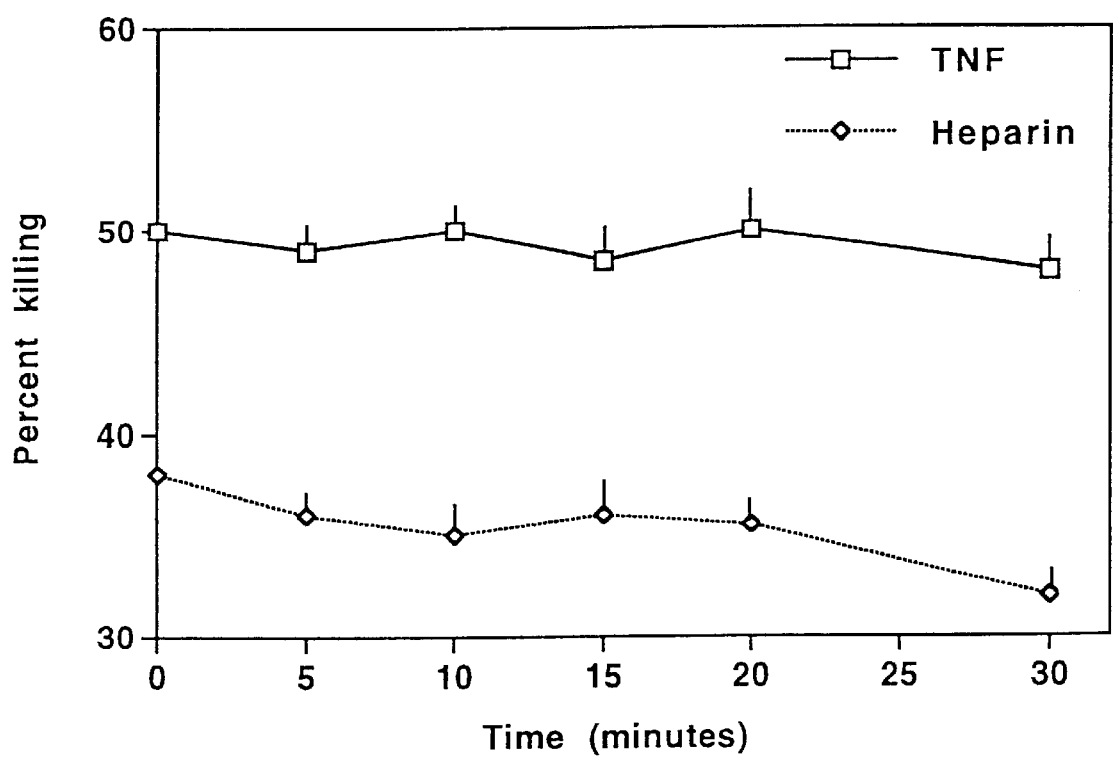
FIG. 2 is a graph showing the effect of pretreatment of cells with heparin on TNF cytotoxicity as a function of time the cells were exposed to heparin prior to TNF addition that heparin was added.

Heparin is believed to interfere with the cellular binding of TNF. As detailed in Example 3, WISH cells were pretreated with heparin between 0 and 30 minutes prior to TNF addition. This pretreatment substantially inhibited TNF cytotoxicity, as shown in FIG. 2. The heparin inhibitory effect was expressed immediately (at time 0), suggesting that it is not due to a metabolic effect which induces cell resistance to TNF.

The possible explanations of this phenomenon are:

(1) Heparin may bind to TNF receptors (cell surface or soluble receptors), interfering with the binding of TNF to its receptors.

(2) Heparin does not affect TNF receptors. It may complex with TNF the moment it is applied, and/or may interfere with ligand binding to cell-associated receptors and prevent TNF from inducing receptor trimerization, which is a prerequisite for signal transduction.

As seen in Example 4, elimination of heparin or low molecular weight heparin from supernatant instantaneously eliminates their protective effect against TNF cytotoxicity. Thus, the presence of heparin or a low molecular weight heparin is required for inhibiting TNF activity. The polysaccharides do not induce a metabolic state of resistance in cells pretreated with these polysaccharides. There is no affinity between heparin or low molecular weight heparin and cell membrane elements, such as TNF receptors, since simple mechanical washing practically removes it and abolished the TNF-inhibitory effects.

It may, therefore, be assumed that, since the "cellular effect" of heparin is removable, it is likely that the TNF-inhibitory effect of heparin is due to its adherence to TNF, preventing its association with the cell membrane TNF-Rs or interfering with it.

As detailed in Example 5, examination of the binding of heparin or Clexane® to the soluble TNF receptors or to the complex TNF/TNF-R revealed the following, with reference to FIGS. 4 and 5:

(1) Preincubation of TNF with heparin or Clexane® for 30 minutes, and their application to the WISH cells, further potentiated their TNF inhibitory effect compared to their applications without preincubation (compare FIGS. 4A, 4B, 5A, 5B, columns 3 vs. 6). There appears to be an interference phenomenon. Following preincubation with heparin or low molecular weight heparin, more TNF is bound to the polysaccharide which may interfere with TNF binding to its cell associated receptors. An alternative explanation is that heparin may promote dissociation of the active trimer into inactive monomers.

(2) While p55 sTNF-R or p75 sTNF-R alone could inhibit about 8–15% of the TNF bioactivity, the addition of either heparin or Clexane® to TNF and either receptor potentiated the inhibition by the receptors 3–4 times (60% inhibition). Compare FIGS. 4 and 5, columns 2, 4 and 5.

Thus, heparin or low molecular weight heparin may augment the soluble TNF-R binding to TNF, potentiating three to four times the neutralizing effect of both p55 sTNF-R and p75 sTNF-R. It appears that the polysaccharide cross-links TNF to its receptors. Although the conclusion that heparin prevents TNF binding to its cell associated receptors and the conclusion that heparin augments this binding to the soluble receptors seems contradictory and paradoxical, both conditions result in an inhibition of TNF bioactivity and may coexist.

(3) Simple preincubation of p55 sTNF-R with TNF, unlike its preincubation with p75 sTNF-R, resulted in superior TNF inhibition, as shown in FIGS. 4A and 5A, and 4B and 5B, comparing columns 4 and 7. This may be related to the "ligand passing" effect of p75 sTNF-R.

(4) Thirty-minute preincubation of TNF with p55 sTNF-R/p75 sTNF-R and heparin/Clexane® resulted in almost the same TNF inhibition observed when the three components were applied over cells without preincubation (cf. FIGS. 4 and 5, comparing columns 5 to 8). From this, one can conclude that the interaction among TNF, soluble receptor, and heparin is instantaneous, unlike the interaction of TNF-heparin, which is augmented with time, as shown above. This suggests that the natural tendency of TNF to bind instantaneously to its receptor may be followed by quick cross-linking of the complex formed by heparin/Clexane®.

(5) TNF was preincubated with heparin/Clexane® for thirty minutes and just prior to their application to cells, the p55 sTNF-R or p75 sTNF-R, respectively, was added. The observed TNF cytotoxicity was higher compared to the simultaneous preincubation of the three components, as shown in FIGS. 4 and 5, comparing columns 8 to 9. One explanation is that, during the TNF+heparin/Clexane® incubation, the polysaccharide complexed with TNF, interfering with its binding to the soluble receptors upon their later addition. Since free TNF, heparin, and their complex were at equilibrium, elimination of free TNF by addition of soluble receptors resulted in dissociation of TNF/polysaccharide complexes in order to regain the equilibrium, and free TNF had an equal chance to bind the soluble receptors of the cell receptors and activate them. Further support for heparin/Clexane®'s interference with TNF binding to its receptor was gained when comparing column 9 to column 5 in FIGS. 4 and 5.

(6) Thirty-minute preincubation of p55 sTNF-R or p75 sTNF-R with either heparin/Clexane® and addition of TNF just before application to the cells, as shown in FIGS. 4A and 5A, and 4B and 5B, resulted in TNF inhibition identical to that obtained if the three components were added simultaneously to cells (column 5) or after their joint preincubation for thirty minutes (column 8). From this it can be concluded that the polysaccharide does not interfere with TNF-receptor binding to TNF, and has no affinity for the "bare" TNF receptor. However, heparin/Clexane® has a strong affinity for the TNF/TNF-receptor complex, which it avidly cross-links. Thus, since heparin/Clexane® has no affinity for the "bare" soluble TNF receptors, the ease of washing of the "cellular effect" of heparin/Clexane®, shown in FIG. 2, is consistent with the conclusion that the heparin/Clexane® has no affinity for the "bare" cell associated receptors as well.

Figure 4A:
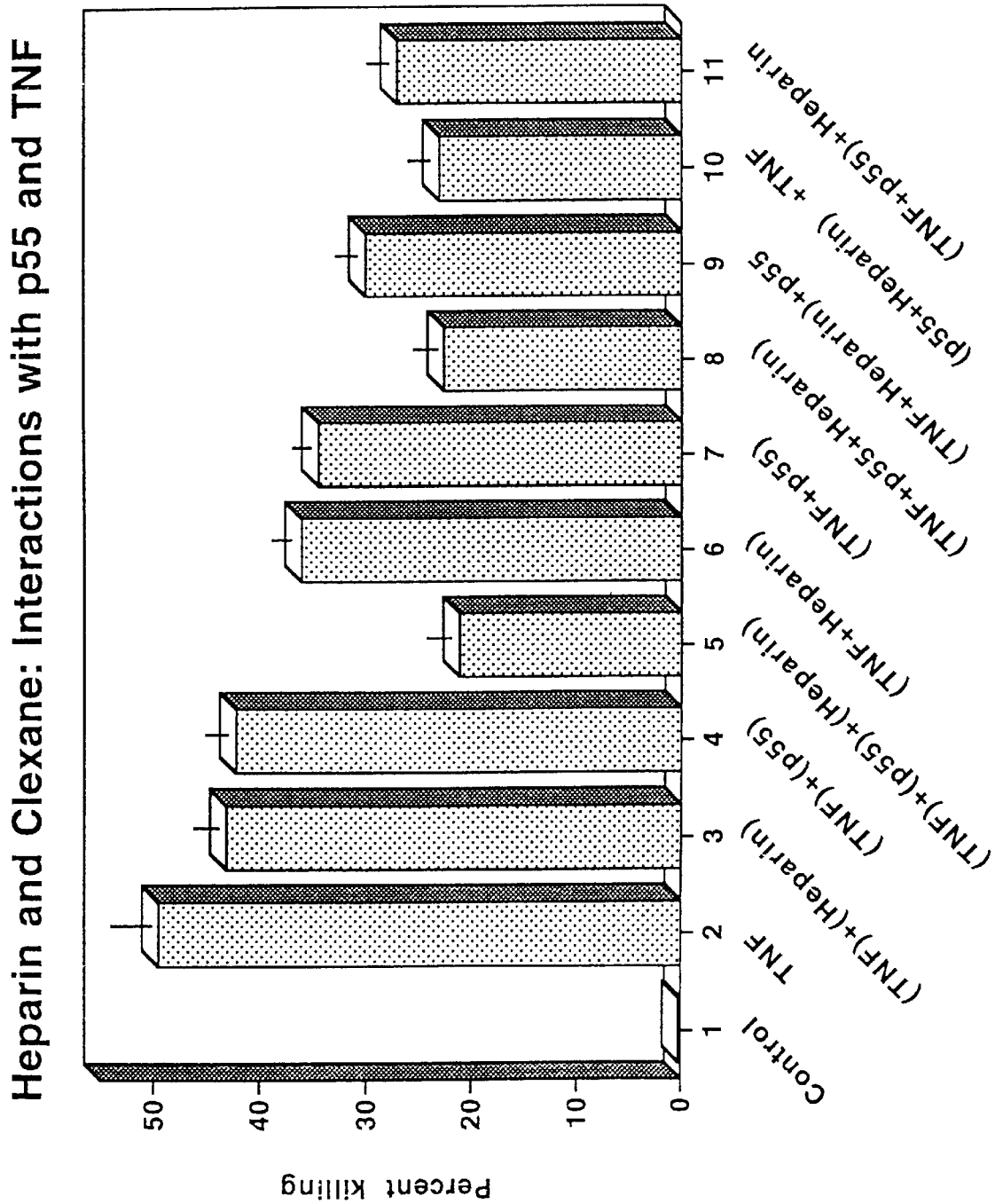
FIG. 4A shows the interactions of heparin with p55 sTNF-R and TNF.
Figure 4B:
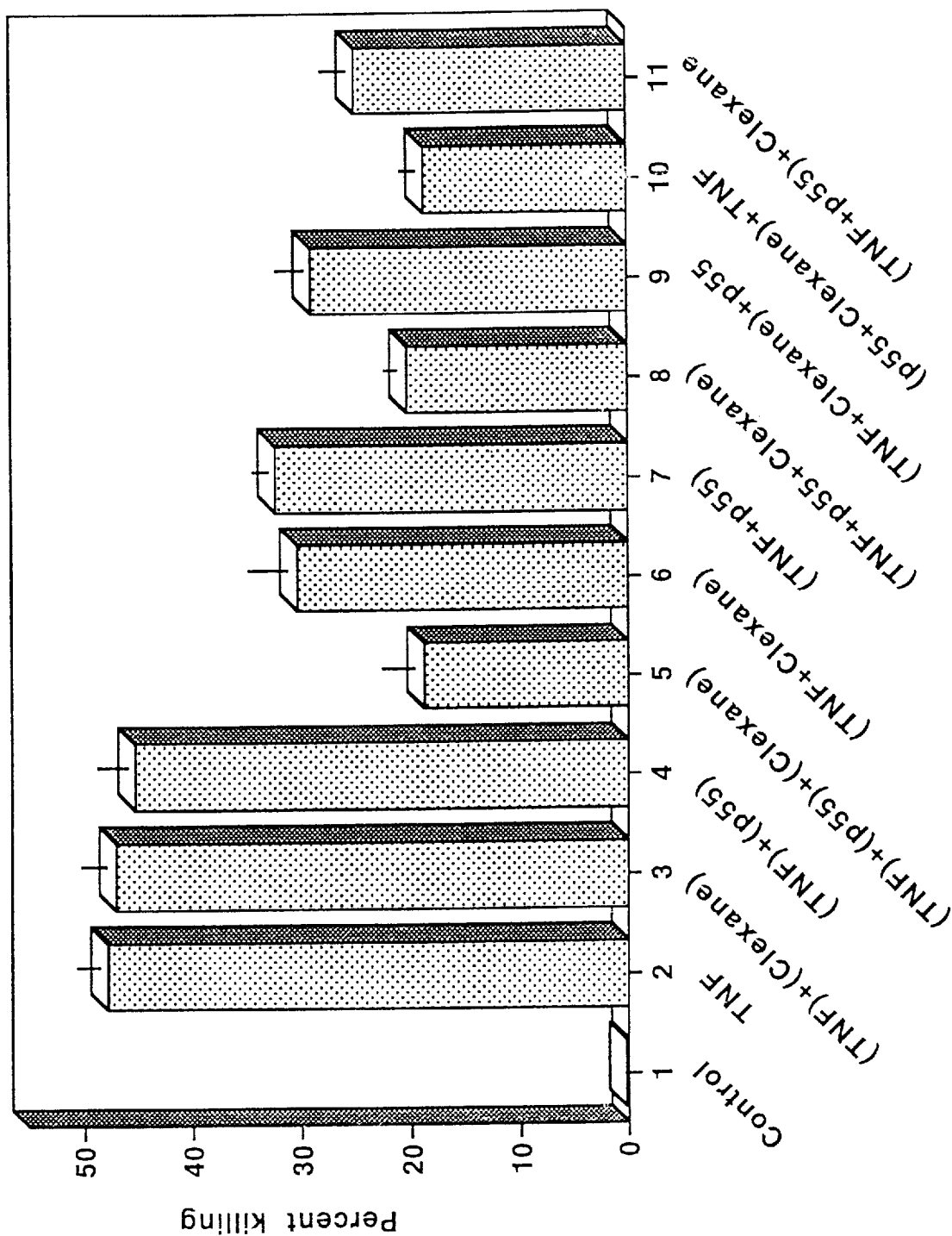
FIG. 4B shows the interactions of Clexane® with p55 sTNF-R and TNF.

(7) The inhibition of TNF after its preincubation with its p55 sTNF-R and addition of heparin/Clexane® just before application to cells was better (FIGS. 4A and 4B, column 11) than the inhibition obtained after TNF preincubation with p55 sTNF-R only, as shown by a comparison of FIGS. 4A and 4B, columns 7 and 11. This suggests that heparin/Clexane® further facilitates the inhibition of TNF by p55 sTNF-R, probably by their cross-linking. It should be noted that following heparin/Clexane® addition, the TNF inhibition by p75 sTNF-R was better (20–25%) than the inhibition of p55 sTNF-R (15%). This can be seen by comparing FIGS. 4A and 4B, columns 7 and 11, with FIGS. 5A and 5B, columns 7 and 11. Heparin/Clexane® potentiates TNF binding to its p55 sTNF-Rr and p75 sTNF-R. The greater TNF inhibition by p75 sTNF-R in the presence of the polysaccharide may be related to prevention of "ligand passing" by p75 sTNF-R when heparin/Clexane® cross-links it to TNF.

Heparin/Clexane® potentiates binding of TNF to its soluble receptors, thus augmenting their TNF inhibitory effect. However, one would expect that a similar enhanced binding to cell associated receptors, shown in FIGS. 4 and 5, comparing column 2 to column 3, would result in enhanced TNF cytotoxicity. In practice, though, TNF's cytotoxicity was inhibited.

One theoretical explanation for this apparent paradox is that heparin/Clexane® promotes cross-linking of the bioactive TNF trimer to only one or two TNF receptors, thus interfering with the binding of the third receptor to it. Promoting such binding to soluble TNF receptors neutralizes TNF bioactivity. Obviously, potentiating TNF binding to only one or two cell surface receptors, while interfering with the final receptor aggregation into trimers, explains the above paradox, as signal transduction is best elicited upon aggregation of three cell surface receptors. Following cross-linking of one cell surface receptor to TNF by heparin/Clexane®, the polysaccharide may become interposed in a way that may prevent further cell surface TNF-receptor trimerization. On the other hand, if the TNF already induced receptor trimerization, heparin cannot cross-link this complex or interfere with its function. This may be the key to TNF inhibition by this polysaccharide.

In support of the above explanation, it was noted that there was a paradoxical effect in the experiments. In experiments where lower amounts of soluble receptors were used, characterized by a minimal (less than 10% TNF inhibition), the potentiating effect of heparin/Clexane® was maximal (more than 60% inhibition). In experiments in which the receptors exerted a 50% inhibition, heparin/Clexane® had a marginal potentiating effect.

It appears that with very low amounts of soluble receptors, most TNF trimers can produce complexes with only one soluble receptor. These complexes are the probable target of heparin/Clexane® cross-linking, resulting in a remarkable TNF inhibition. If the amount of the soluble receptors is higher, two or more soluble receptors may bind to TNF, preventing their effective cross-linking of such complexes by the polysaccharide. It remains to be demonstrated that these complexes are not stabilized by heparin/Clexane® to the same extent as are complexes of TNF and monomeric soluble receptor.

Strong supporting evidence that the heparin/Clexane® cross-linking may be limited to complexes of TNF with one or, at most, two receptors comes from comparison of columns 5 to 11 of FIGS. 4 and 5. If an equilibrium was attained between TNF+p55 sTNF-R with formation of TNF complexes with one, two or three receptors, and then heparin/Clexane® was added (column 11), the TNF cytotoxicity was enhanced compared to simultaneous addition of the TNF, its receptors and heparin over cells (column 5). A possible explanation is that, in the latter situation, TNF could initially bind one single receptor. This complex would be immediately cross-linked by heparin/Clexane®, preventing TNF from binding a second or third receptor.

Figure 6A:
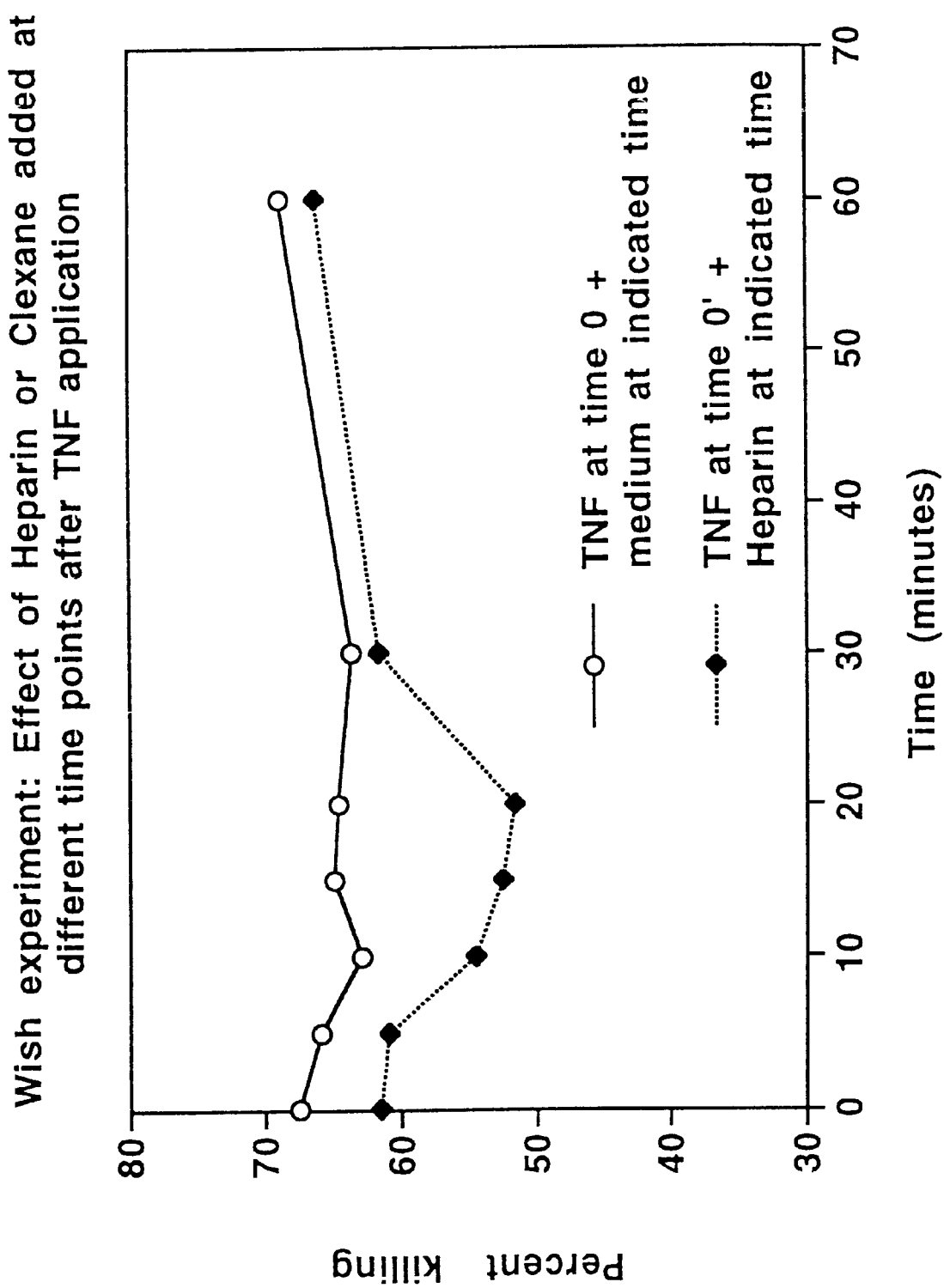
FIG. 6A shows the effect of heparin added at different time points after TNF application.
Figure 6B:
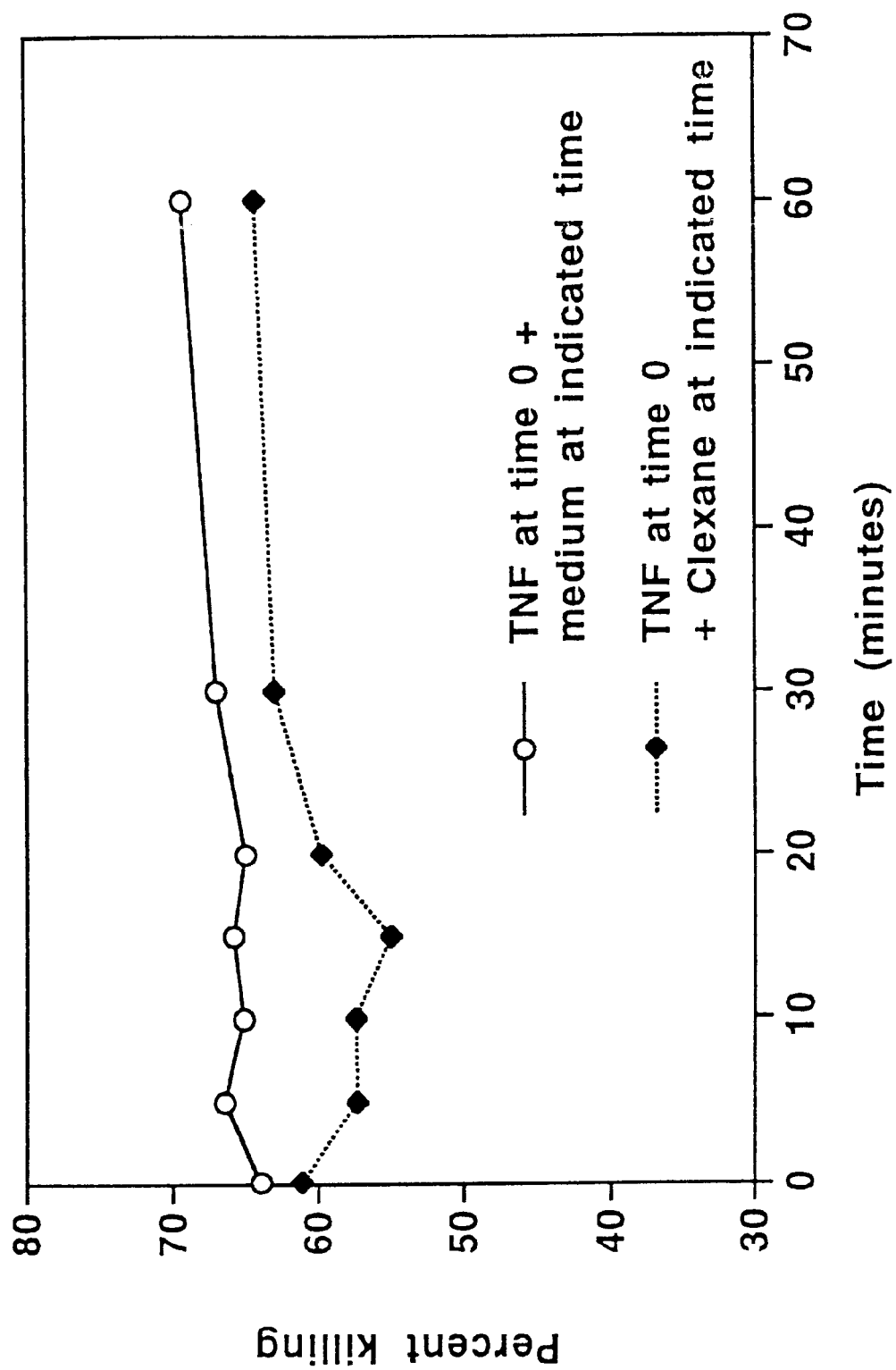
FIG. 6B shows the effect of Clexane® added at different time points after TNF application.
Figure 7:
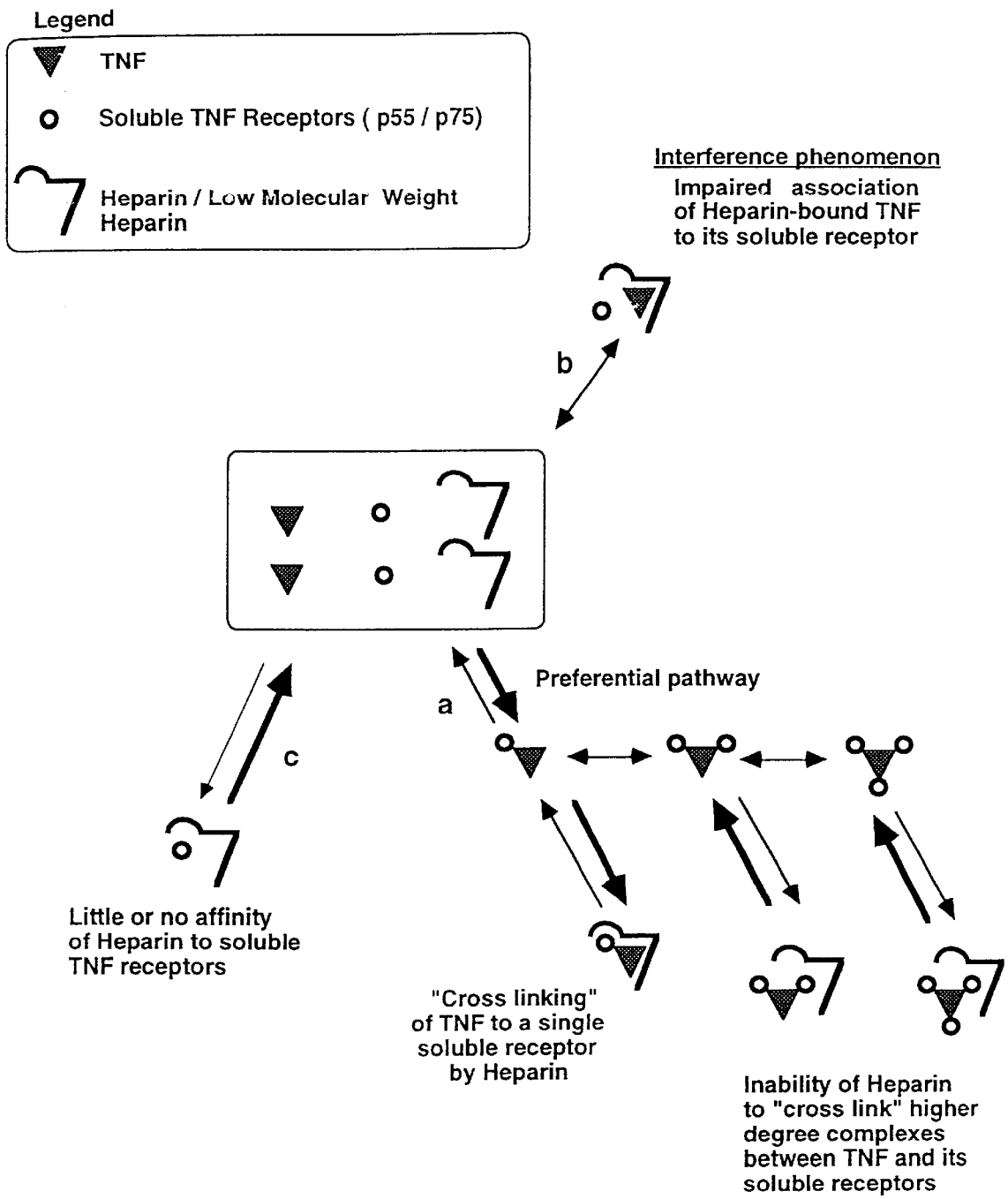
FIG. 7 illustrates interactions between TNF, soluble TNF-receptors, and heparin or low molecular weight heparin.
Figure 8:
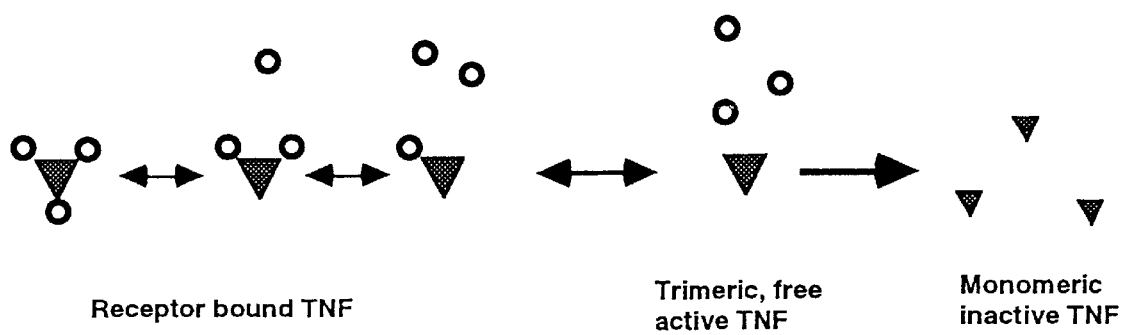
FIG. 8 shows the equilibrium between TNF and its soluble receptors.

Additional supporting evidence can be found in the experiment to determine if heparin/Clexane® can inhibit the bioactivity of TNF if heparin/Clexane® is added after TNF application. If heparin/Clexane® was applied at different time periods after TNF application, its inhibitory activity was still significant after 15 minutes, and marginally persistent after one hour. Surprisingly, in two experiments, the inhibitory activity of heparin/Clexane® was about 7–15% at time 0, increased to 25% if applied 5–15 minutes after TNF, and decreased to 10% at one hour (FIG. 6).

One explanation for this paradoxical increase if heparin/Clexane® is added 5–15 minutes after TNF is that heparin/Clexane® binds avidly only one monomer-receptor to a trimer TNF. This binding interferes with further receptor trimerization, which is known to be followed by signal transduction.

One can visualize the binding of TNF to its receptors as a process during which, at the beginning, TNF is bound to one receptor, with time is bound to the second receptor, and with additional time to the third receptor. The fact that heparin/Clexane® can still inhibit TNF even one hour after its application suggests that it may interfere at this late stage with trimerization of the few last receptors. TNF molecules may be combined at this later stage with one receptor or two, and heparin/Clexane® interferes with the binding of the third, which would otherwise induce signal transduction.

This mechanism may explain the paradox that addition of heparin/Clexane® fifteen minutes following TNF application results in a better inhibition of TNF than when applied simultaneously. At time 0, heparin/Clexane® binds part of the TNF and may slightly interfere with its binding to the cell receptors, as noted above. If low concentrations of TNF are applied several minutes before heparin/Clexane®, TNF has the opportunity to bind to its receptors undisturbed, and application of the heparin now will cross-link optionally the TNF bound to receptor monomers.

It can thus be seen that treating a patient with heparin and/or a low molecular weight heparin can inhibit the bioactivity of TNF. The effect of heparin or derivatives thereof can be potentiated by administering p55 sTNF-R or p75 sTNF-R in combination with the heparin or derivative thereof. The heparin and soluble receptors can be administered simultaneously, or over approximately a 15–30 minute interval. Alternatively, the heparin or derivative is administered, and approximately 15–60 minutes later p55 sTNF-R or p75 sTNF-R is administered.

While heparin per se can be administered, low molecular weight heparin, produced by fractionation or controlled depolymerization of heparins, has improved antithrombotic performance, as well as different pharmacokinetic properties, as compared to heparin. The half-life of the low molecular weight heparins is doubled. However, even though Bratt et al (1985) found that their bioavailability is higher with respect to their anticoagulant effect after subcutaneous injection, it should be noted from FIGS. 4 and 5 that heparin and Clexane® interact with p55 sTNF-R, p75 sTNF-R, and TNF approximately the same. Thus, any low molecular weight heparin can be used in place of heparin for the purpose of the present invention.

The low molecular weight heparins that can preferably be used in the present invention include Clexane®, as described above, as well as Fragmin®, a low molecular weight heparin with average molecular weight within the range of 4000–6000 daltons, produced by controlled nitrous acid depolymerization of sodium heparin from porcine intestinal mucosa, manufactured by Kabi Pharmacia, Sweden. Also useful are Fraxiparin® and Fraxiparine®, low molecular weight heparins with average molecular weight of approximately 4500 daltons, produced by fractionation or controlled nitrous acid depolymerization, respectively, or calcium heparin from porcine intestinal mucous manufactured by Sanofi (Choay Laboratories).

For purposes of the present invention, heparin per se can be used, either alone or in combination with a low molecular weight heparin, regardless of the manufacturing process, the structural differences (created by depolymerization or those dependent on variation in the heparin used as raw material), or the anticoagulant activity. Alternatively, a low molecular weight heparin can be used alone.

The disorders that can be treated by inhibiting TNF activity according to the present invention are all disorders related to the presence of TNF and which respond to inhibition of the bioactivity of TNF. Among these disorders are atherosclerosis and vasculitis and pathological processes related thereto; autoimmune diseases, such as rheumatoid arthritis, diabetes mellitus type I; allergies; graft rejection; acute and chronic inflammatory diseases, such as uveitis and bowel inflammation; anorexia nervosa; hemorrhagic shock caused by septicemia; and opportunistic infections in AIDS-compromised individuals.

Heparin or a low molecular weight lieparin, or mixtures thereof, is incorporated into pharmaceutical compositions, for example, as water solutions, possibly comprising sodium chloride, stabilizers, and other suitable non-active ingredients. The preferred method of administration is by injection, subcutaneous or intravenous, but any other suitable mode of administration is encompassed by the invention.

The soluble TNF receptors, p55 sTNF-R and p75 sTNF-R, are likewise incorporated into pharmaceutical compositions, either alone or in combination with heparin and derivatives thereof. The amounts of heparin or derivatives thereof administered depend upon the mode of administration. If a slow release preparation is administered, the amounts administered will be much lower than if administered intramuscularly or intravenously.

Pharmaceutical compositions for administration according to the present invention can comprise at least one heparin or derivative thereof and at least one soluble TNF receptor, either separately or together, in a pharmaceutically acceptable form optionally combined with a pharmaceutically acceptable carrier. These compositions can be administered by any means that achieve their intended purposes. Amounts and regimens for the administration of a composition according to the present invention can be determined readily by those with ordinary skill in the art of treating disorders related to excessive bioactivity of TNF.

For example, administration can be by parenteral, such as subcutaneous, intravenous, intramuscular, intraperitoneal, transdennal, or buccal routes. Alternatively or concurrently, administration can be by the oral route. The dosage administered depends upon the age, health and weight of the recipient, type of previous or concurrent treatment, if any, frequency of the treatment, and the nature of the effect desired.

Compositions within the scope of this invention include all composition comprising at least one heparin or derivative administered in combination with at least one soluble TNF receptor in an amount effective to achieve its intended purpose. While individual needs vary, determination of optimal ranges of effective amounts of each component is within the skill of the art. Typical dosages comprise about 0.1 to about 100 mg/kg body weight.

The following non-limiting examples will help to explain the present invention.

EXAMPLE 1

Inhibition of TNF Activity by Heparin

WISH cells were seeded at a concentration of 30,000 cells/well in 100 µl medium. Sixteen hours later, either medium (control), heparin, TNF or a combination of TNF plus heparin was added. The final concentrations of each into the respective wells were as follows: TNF 0.5 ng/ml; heparin 1 unit/ml. After the various additions, cyclohexamide was added to each well (50 μl) for a final concentration of 25 μg/ml in the well. Sixteen hours later, the cell supernatants were discarded and neutral red dye was added for one hour. Following the one hour incubation, the dye was extracted with a Sorensen's solution, and the results were read in an ELISA reader. The results directly correlate with percent of cell killing. The results are shown in FIG. 1A. It can be seen that the addition of TNF inhibits about 25% of the bioactivity of TNF (reduction of cytotoxicity from 49% to 37%).

EXAMPLE 2

Inhibition of TNF Activity by Clexane®

The same procedure as in Example 1 was repeated except that Clexane® was substituted for heparin. The results are shown in FIG. 1B. It can be seen that substantially similar inhibitory effects are obtained.

EXAMPLE 3

Effect of Pre-Treatment with Heparin on TNF Cytotoxicity

The same procedure as in Example 1 was repeated except that the WISH cells were treated with heparin between 0–30 minutes before addition of the TNF. The results are shown in FIG. 2. It can be seen that substantially identical inhibitory effects are obtained throughout the timeline.

EXAMPLE 4

Effect of Heparin Removal by Washing

Figure 3A:
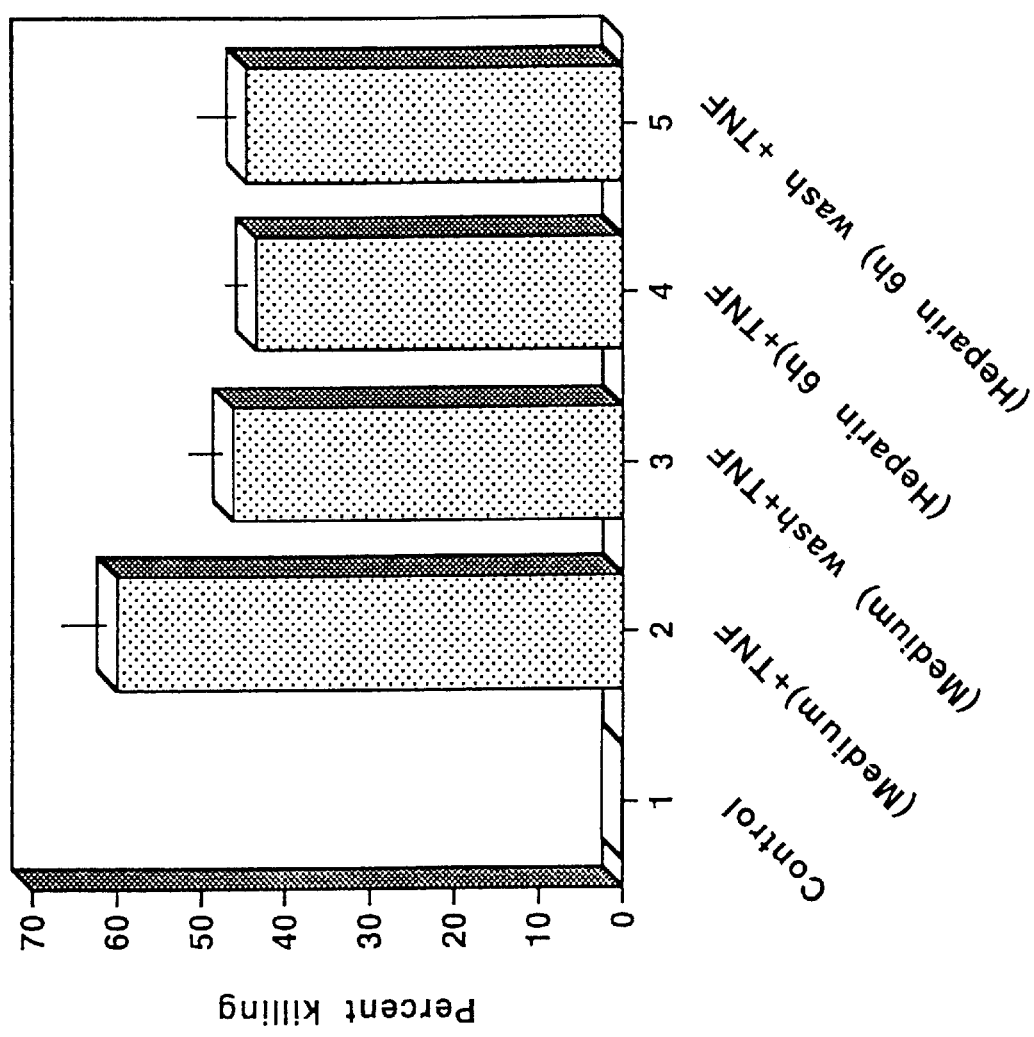
FIGS. 3A and 3B show the influence of supernatant removal on the cytotoxic effect of TNF.
Figure 3B:
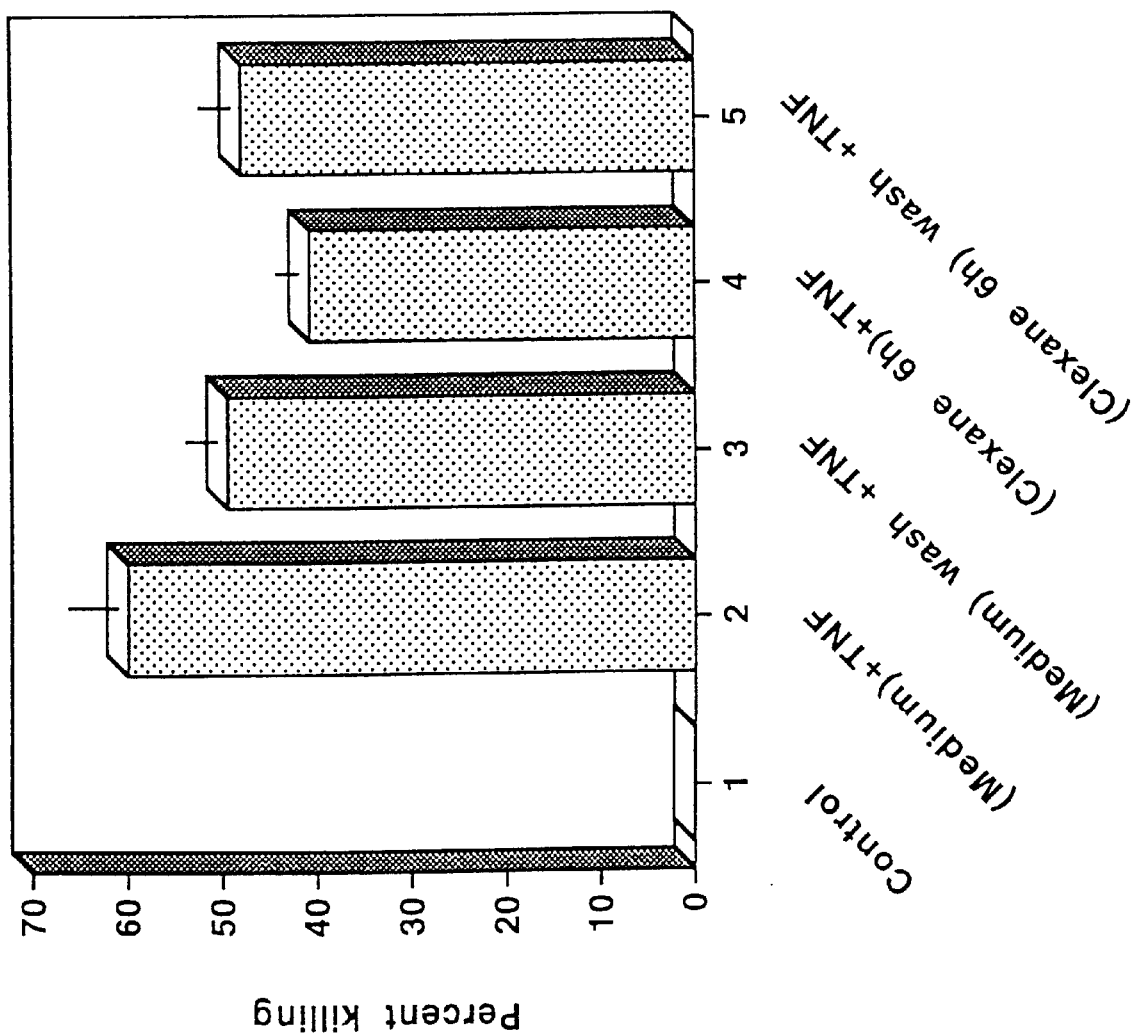

WISH cells were seeded at a concentration of 30,000 cells per well in 100 μl medium. Sixteen hours after seeding of the cells either heparin or Clexane® was added to respective wells, while medium alone was added to control wells. The heparin or Clexane® was added to a final concentration of 1 unit/ml. Six hours later, part of the wells pretreated with either heparin or Clexane® or with medium only were washed three times with fresh medium, and TNF was added to a final concentration of 0.5 ng/ml. The results are shown in FIG. 3A for heparin and FIG. 3B for Clexane®. It can be seen that heparin/Clexane® pretreatment reduced the TNF cytotoxicity by 33% as expected (from 60% to 40%) (compare columns 2 to 4 in FIGS. 3A and 3B). However, simple washing of the cells treated with medium also resulted in a 25% reduction in the cell susceptibility to TNF. Cells pretreated with heparin or Clexane®, whose supernatants were washed before TNF addition, had an identical killing by TNF (compare columns 3 to 5 of FIGS. 3A and 3B). Thus, elimination of heparin or Clexane® from the supernatants eliminates instantaneously their protective effect against TNF cytotoxicity.

Removal of the supernatants, washing the cells and addition of new medium increases the cell resistance to TNF by 20%. It is possible that the removed supernatants contain a factor that facilitates TNF cytotoxicity and its elimination reduces the effect of TNF. Another possibility is that, following removal of the supernatants, there is rapid shedding of the cell surface TNF receptors, as previously found (Aderka, in press), which may induce some transient desensitization to TNF.

EXAMPLE 5

Effect of Heparin/Clexane® on TNF Receptors

WISH cells were seeded at a concentration of 30.000 cells/well in 100 μl medium. Sixteen hours later, either medium alone (control), or sTNF-R (either p55 sTNF-R (FIGS. 4A and 4B) or p75 sTNF-R (FIGS. 5A and 5B)), and either heparin (FIGS. 4A and 5A) or Clexane® (FIGS. 4B and 5B) were added. The final concentrations of each in the respective wells were as follows: TNF 0.5 ng/ml; heparin 1 unit/ml; Clexane® 1 unit/ml; TBP-I (p55 TNF-receptor) 5 ng/ml; TBP-II (p75 TNF-receptor) 10 ng/ml.

Different combinations of the ingredients were mixed in an Eppendorf tube reaching a final volume of 300 μl. 50 μl were then added to each respective well. If an incubation was required, it was done in an Eppendorf tube as a mixture or separately for 30 minutes at 37° C.

After addition of the different combinations, cyclohexamide was added to each well (50 μl) for a final concentration of 25 μg/ml. Sixteen hours later, the cell supernatants were discarded and neutral red dye was added for one hour. Following the one hour incubation, the dye was extracted with a Sorensen's solution and the results were read in an ELISA reader.

The results are shown in FIGS. 4A, 4B, 5A and 5B. In each of these figures, the first bar of the graph represents a control in which the Eppendorf tube included 300 pi of medium only. In the second bar of each, the Eppendorf tube included 2.1 μl of TNF at a concentration of 2 ng/ml plus 20 μl of medium.

In bar 3 of each figure, 1.8 units of either heparin or Clexane® (10 μl) and 10 μl of medium were added to the Eppendorf tube along with the addition of 280 μl of TNF at a concentration of 2.1 ng/ml. The mixture was then immediately added to the WISH cell wells.

Figure 5A:
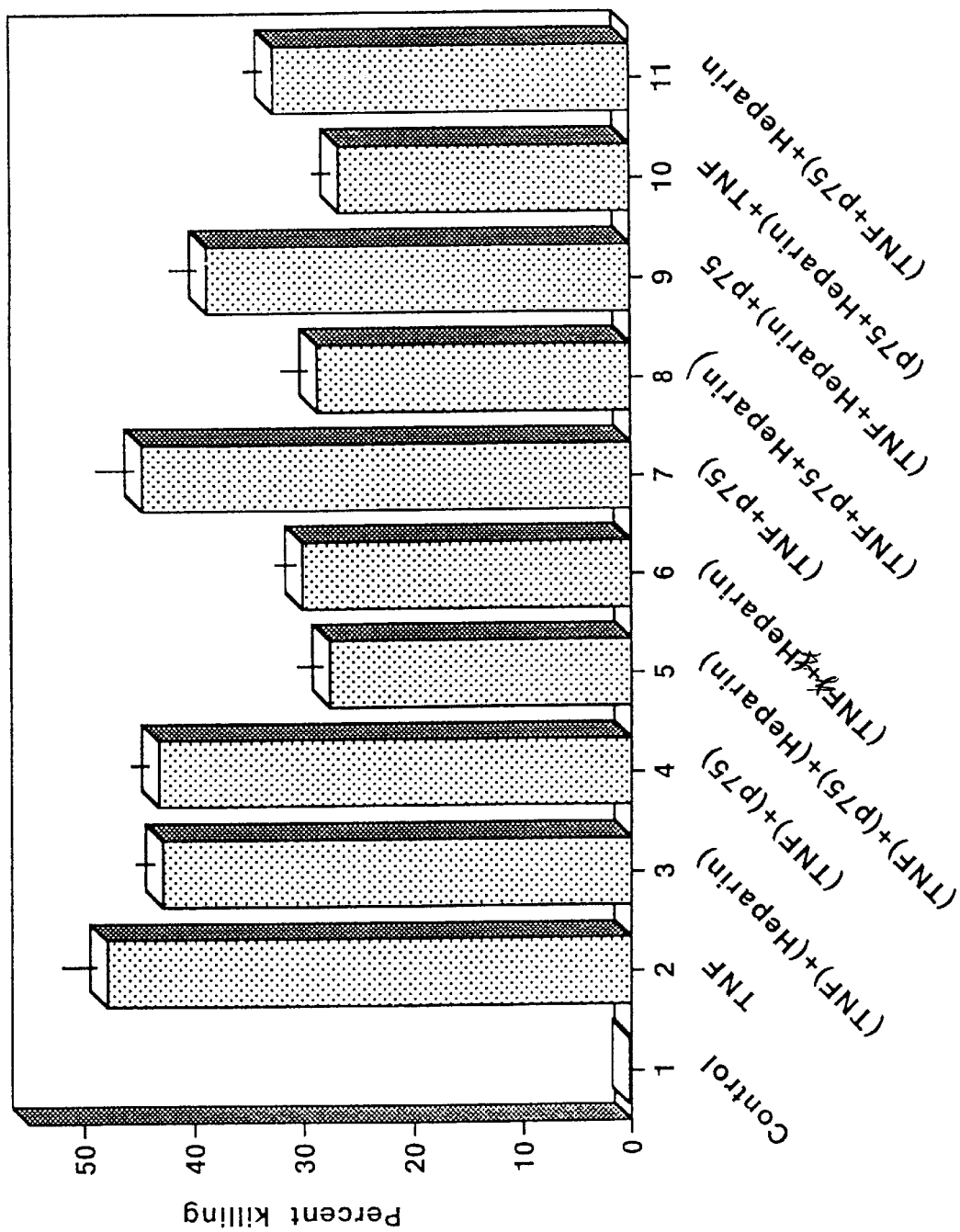
FIG. 5A shows the interaction of heparin with p75 sTNF-R and TNF.
Figure 5B:
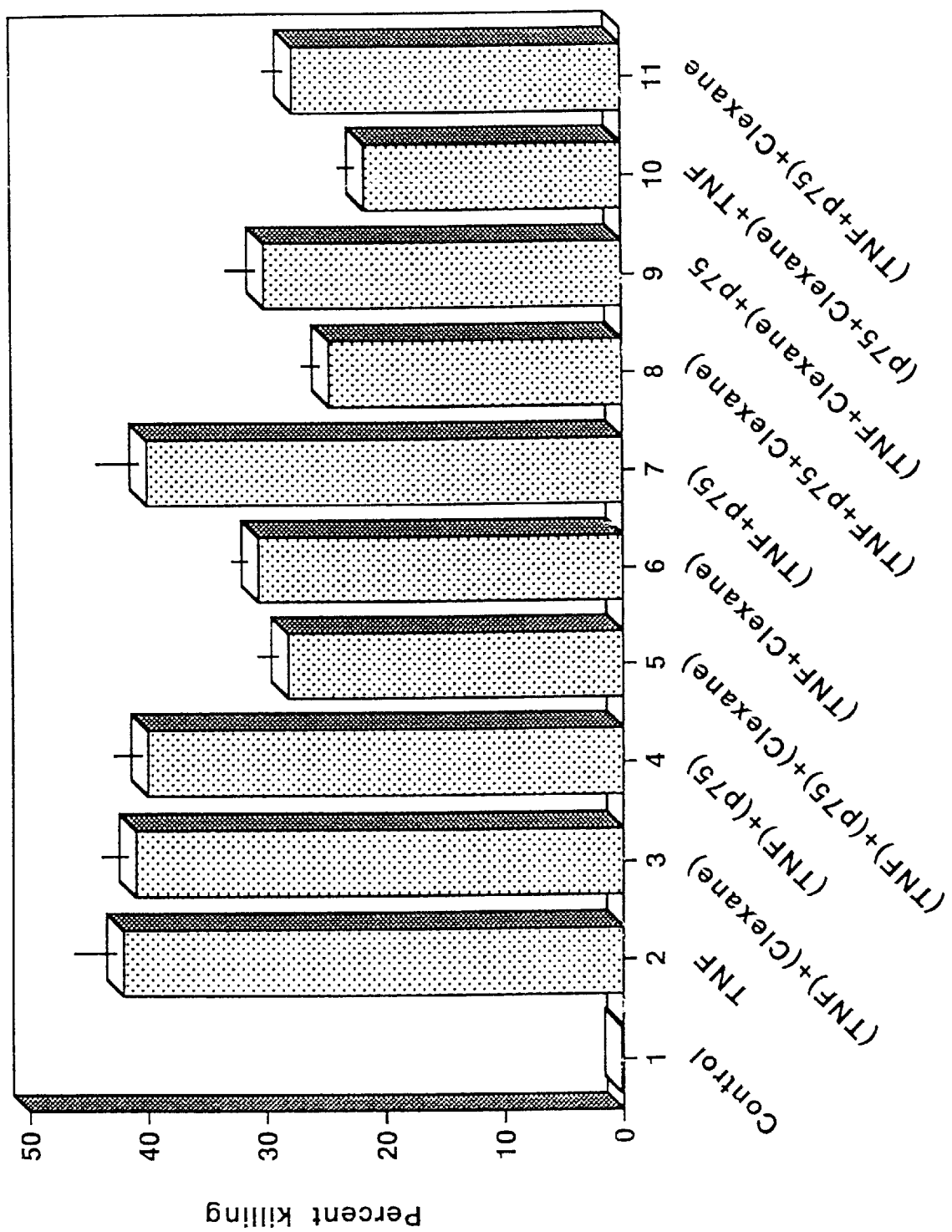
FIG. 5B shows the interactions of Clexane® with p75 sTNF-R and TNF.

With respect to the fourth bar, 6 ng p55 sTNF-R (10 μl) were added to 10 μl of medium and the same amount of TNF discussed above, immediately prior to addition of to the WISH cell wells. In FIGS. 5A and 5B, double the amount of p75 sTNF-R (12 ng/10 μl) was used in place of p55 sTNF-R.

With respect bar 5, 6 ng of p55 sTNF-R or 12 μg of p75 sTNF-R (10 μl), 1.2 units of either heparin or Clexane® (10 μl), and 280 μl TNF at 2.1 ng/ml were added to the Eppendorf tube. The mixture was then immediately added to the WISH cell wells.

Bar 6 involves the same materials as discussed above for bar 3, except that the TNF and either heparin or Clexane® were added simultaneously to the Eppendorf tube and then incubated together for 30 minutes prior to being added to the WISH cell wells. Similarly, bar 7 is the same as described above for bar 4, except that either the p55 sTNF-R or p75 sTNF-R was mixed with the TNF and incubated together for 30 minutes at 37° C. before being added to the WISH cell wells. The experiment of bar 8 is the same as that described above for bar 5, except that the TNF, either the p55 sTNF-R or the p75 sTNF-R, and either the heparin or Clexane® were mixed together and incubated for 30 minutes before being added to the WISH cell wells.

For bar 9, the TNF and either heparin or Clexane® were pre-incubated together for 30 minutes before addition of either the p55 sTNF-R or p75 sTNF-R which were pre-incubated separately and then immediate addition to the WISH cell wells. For bar 10, either the p55 sTNF-R or the p75 sTNF-R and either the heparin or Clexane® were pre-incubated together for 30 minutes before addition of the pre-incubated TNF and then immediate addition to the WISH cell wells. For bar 11, the TNF and either p55 sTNF-R or p75 sTNF-R were incubated together for 30 minutes before addition of either the pre-incubated heparin or Clexane® and then immediate addition to the WISH cell wells.

As can be seen from a comparison of the various bars of FIGS. 4A, 4B, 5A and 5B, pre-incubation of TNF with heparin/Clexane® for 30 minutes and their application to the WISH cells further potentiated their TNF inhibitory effect compared to their application without pre-incubation (comparing bars 3 and 6 of each). Furthermore, while p55 sTNF-R or p75 sTNF-R alone could inhibit about 8–15% of the TNF bioactivity, addition of either heparin or Clexane® to TNF and either receptor potentiated the inhibition by the receptors three to four times (60% inhibition) (comparing columns 2, 4 and 5 of the various figures).

Kits for the simultaneous or sequential administration of heparin and/or a derivative thereof, and a soluble TNF receptor, are prepared in a conventional manner. Typically, such a kit will comprise, e.g. an ampoule of each of the active ingredients in a pharmaceutically acceptable carrier, a syringe, and written instructions for the simultaneous or sequential administration. For example, if simultaneous administration is desired, the contents of the ampoules may be mixed prior to injection in either a suitable vessel, or in the syringe itself.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same function can be used; and it is intended that such expressions be given their broadest interpretation.

REFERENCES

Abraham et al, *JAMA* 273:934–941 (1995)
Aderka et al, *J. Exp. Med.* 175:323–329 (1992)
Aderka, *J. Clin. Invest.* (in press)
Aggarwal et al, *Eur. Cytokine Netw.* 7:93–124
Ashkenazi et al, *Proc. Natl. Acad. Sci.* 88:10535–10539 (1991)
Bigda et al, *J. Clin. Invest.* 88:2026–2031 (1991).
Bone et al, *Thrombosis Research* 46:845 (1987)
Braegger et al, *Lancet* 329:89–91 (1992)
Bratt et al, *Thrombosis and Haemostasis* 53:208 (1985)
Breese et al, *Gastroenterology* 106:1455–1466 (1994)
Cope et al, *Arthritis and Rheumatism* 35:1160–1169 (1992).
Cunnion, R. E., *Ann. Intern. Med.* 113:227–242 (1990)
De Groote et al, *Eur. Cytokine Netw.* 4:359–362 (1993)
De Meules et al, *J. Trauma* 32:686–692 (1992)
Eliaz et al, *Eur. Cytokine Netw.* 7:291 (abstract) (1966)
Elliot et al, *Lancet* 344:1105–1110 (1994)
Engelmann et al, *J. Biol. Chem.*, 264:119974–11980 (1989)
Englemann et al, *J. Biol. Chem.* 265:1531–1536 (1990)
Evans et al, *J. Exp. Med.* 180:2173–2179 (1994)
Fisher et al, *New Engl. J. Med.* 334:1697–1702 (1996)
Girardin et al, *Immunol.* 76:20–23 (1994)
Kaul et al, *Eur. Cytokine Netw.* 7:283 (abstract) 1996)
Lantz et al, *J. Clin. Invest.* 88:2026–2031 (1991)
Leighton et al, *Eur. Cytokine Netw.* 7:282 (abstract) (1996)
Lesslauer et al, *Eur. J. Immunol.* 21:2883–2886 (1991)
Levine et al, *New Engl. J. Med.* 323:236–241 (1990)
Lider et al, *J. Clin. Invest.* 83:752–757 (1989)
Lider et al, *Eur. J. Immunol.* 20:493 (1990)
Loetscher et al, *Cancer Cells* 3:221–226 (1991)
MacDonald et al, *Clin. Exp. Immunol.* 81:301–305 (1990)
Mohler et al, *J. Immunol.* 151:1548–1561 (1993)
Naparstek et al, *Nature* 310:231–243 (1984)
Nophar et al, *The EMBO J.* 9:3269–3278 (1990)
Olsson et al, *Eur. J. Haematol.* 42:270–275 (1989)
Peppel et al, *J. Exp. Med.* 174:1483–1489 (1991)
Petersen et al, *Eur. J. Immunol.* 19:1887–1891 (1989)
Roux-Lombard et al, *Arthr. Rheumat.* 36:485–489 (1993)
Seckinger et al, *J. Biol. Chem.*, 264:11966–11973 (1989)
Suffredini et al, *Ann. Int. Med.* 120:771–783 (1994)
Tartaglia et al, *Immunol. Today* 13:151–153 (1992)
Tracey et al, *Science* 234:470–474 (1986)
van Dullemen et al, *Gastroenterol.* 109:129–135 (1995)

What is claimed is:

1. A composition for inhibiting the bioactivity of TNF, comprising an effective amount of heparin or a low molecular weight derivative thereof, or a mixture of heparin and a low molecular weight derivative thereof, and at least one sTNF-R.

2. A composition according to claim 1, further comprising a pharmaceutically acceptable carrier.

3. A composition according to claim 1, wherein the sTNF-R is selected from the group consisting of p55 sTNF-R and p75 sTNF-R.

4. A composition according to claim 1, wherein the heparin or a low molecular weight derivative thereof is a low molecular weight heparin.

5. A composition according to claim 4, wherein the low molecular weight heparin has a molecular weight between 2500 and 6500 daltons.

6. A kit for the simultaneous or sequential administration of a composition according to claim 1, comprising the active ingredients together with a pharmaceutically acceptable carrier, and instructions for use.

7. A composition comprising heparin and/or a low molecular weight derivative thereof and a sTNF-R.

8. In a method for inhibiting the activity of TNF in a subject comprising treating said subject with an effective amount of sTNF-R, the improvement whereby the effect of sTNF-R is potentiated comprising treating said subject with a combination of said sTNF-R with an amount of heparin or a low molecular weight derivative or a mixture of heparin and a low molecular weight derivative thereof, said amount being effective to potentiated the effect of said sTNF-R.

9. A method in accordance with claim 8, wherein said sTNF-R is selected from the group consisting of p55 sTNF-R and p75 sTNF-R.

10. A method in accordance with claim 9, wherein said heparin or low molecular weight derivative thereof is administered simultaneously with said sTNF-R.

11. A method in accordance with claim 9, wherein said heparin or low molecular weight derivative thereof is administered within one hour after administration of said sTNF-R.

12. A method in accordance with claim 8, wherein said heparin or low molecular weight derivative thereof is a low molecular weight heparin.

13. A method in accordance with claim 12, wherein said low molecular weight heparin has a molecular weight between 2500 and 6500 daltons.

* * * * *